United States Patent [19]

Joos

[11] Patent Number: 4,547,363

[45] Date of Patent: Oct. 15, 1985

[54] PREPARATION FOR STRENGTHENING, PARTICULARLY HARDENING, LIVING FINGER NAILS

[76] Inventor: Bernhard Joos, Riva Paradiso 32, 6900 Lugano, Switzerland

[21] Appl. No.: 384,087

[22] Filed: Jun. 1, 1982

[30] Foreign Application Priority Data

Jun. 26, 1981 [CH] Switzerland ............... 4233/81

[51] Int. Cl.⁴ .................. A61K 7/04; A61K 7/06; B65D 69/00
[52] U.S. Cl. .................. 424/61; 424/70; 206/581; 206/812
[58] Field of Search .................. 424/61, 70, 71; 524/714; 106/4; 132/7; 206/581, 812

[56] References Cited

U.S. PATENT DOCUMENTS

| | | | |
|---|---|---|---|
| 3,349,000 | 10/1967 | Joos | 424/61 |
| 3,441,645 | 4/1969 | McKissick et al. | 424/61 |
| 3,725,525 | 4/1973 | Joos | 424/61 |
| 3,749,769 | 7/1973 | Sugiyama et al. | 424/61 |

FOREIGN PATENT DOCUMENTS

| | | | |
|---|---|---|---|
| 1467953 | 1/1969 | Fed. Rep. of Germany | 424/61 |
| 1485602 | 6/1967 | France | 424/61 |
| 1301904 | 1/1973 | United Kingdom | 132/7 |
| 2010296 | 6/1979 | United Kingdom | 424/61 |

*Primary Examiner*—Sidney Marantz
*Assistant Examiner*—Shawn P. Foley

[57] ABSTRACT

Preparation for strengthening, particularly hardening living nails and method of using same which comprises the successive application of two separate product components. The first component contains, as a polymerizable compound, dimethylol ethylene thiourea, a purine, water and an organic solvent or blend of solvents miscible with water, said first component having a pH in the range of between 8 and 10. The second component contains, as a polymerizable catalyst, 0.1N to 0.5N hydrochloric acid, an amino acid, and an organic solvent or blend of solvents miscible with water, said second component having a pH in the range of between 1 and 3.

8 Claims, No Drawings

PREPARATION FOR STRENGTHENING, PARTICULARLY HARDENING, LIVING FINGER NAILS

BACKGROUND OF THE INVENTION

The present invention relates to a new and improved nail protection preparation intended to strengthen, particularly by hardening, living finger and toe nails, and is of the type comprising two separate components, the first of which contains a polymerizable compound and the second of which contains a compound acting as a polymerization catalyst. The invention further pertains to a method of using the novel preparation for the protection of living nails.

It is well known that living nails, which consist of keratin, tend to grow brittle when subjected to the action of organic solvents of the type contained in nail polishes or polish removers, and in washing agents and detergents and other cleaning agents. This brittleness causes the nails to splinter or tear, even when subjected to modest or slight mechanical loads.

A drawback of heretofore known nail protection preparations is that they are effective only for a relatively short period of time, because the protective film is soluble in water, and therefore, very quickly is entirely or partly washed away. Moreover, with some of the conventionally used nail protection preparations—those which are less soluble and cause the formation of a dense protective coat—there exists the risk of asphyxiating the nails unless great care is exercised in applying the protective preparation in a manner which precludes the protective coat from extending to the nail roots. Thus, for instance, in U.S. Pat. No. 3,349,000 there is disclosed a process for the treatment of human nails and hair, wherein the nails or hair are treated with a liquid preparation containing dimethylol thiourea in a quantity of 1 to 15 percent-by-weight based upon the total weight of the product, and about 0.2 to 2 percent-by-weight of a physiologically harmless acid compound selected from the group consisting of phosphoric acid, lactic acid, citric acid, acetic acid, glycerine phosphoric acid and the acid salts of these compounds and a liquid diluent.

In U.S. Pat. No. 3,725,525 there is described a procedure for fortifying living human nails and hair, wherein nails or hair are treated with an effective quantity of dimethylol alkyleneurea or dimethylol alkylene thiourea of the formula

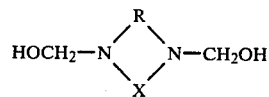

wherein R is an alkylene group containing 2 to 5 carbon atoms, and X is CO or CS. While the results attained with these prior art procedures were better than those obtained with earlier preparations, particularly as regards the elasticity of the treated nails, these methods have failed to achieve a protective effect of long lasting durations, and notably did not harden the nails. In addition, the concentration of urea derivatives of the methylol groups had to be kept very low, in order to reduce to a minimum the quantity of formaldehyde released during the reaction, since formaldehyde is notorious for causing skin irritation, especially allergies.

With the aim of eliminating the noxious effects of free formaldehyde entirely or at least almost completely, U.S. Pat. No. 3,773,056 teaches compositions and procedures for the treatment of degraded hair which use less easily decomposable urea and thiourea derivatives, such as carbamates, guanidines, succinimides, sulphinamides, adipinamides or hydantoins, in order to produce a reaction with organic acids or corresponding acid salts by applying these acids to the hair prior, during or after treatment with urea or thiourea derivatives. This remedy succeeds simply in fortifying or strenghtening human hair inasmuch as it improves its elasticity, but it does not in any way act as a hardener.

OBJECTS OF THE INVENTION

Therefore, with the foregoing in mind it is a primary object of the present invention to provide a new and improved nail protection preparation for strengthening, particularly hardening, living finger nails and a method of use thereof, which is not afflicted with the aforementioned drawbacks and limitations of the prior art proposals.

Another and more specific object of the present invention aims at providing an improved nail protection preparation capable of permanently strengthening living nails, especially by hardening, and which is as free as possible from deleterious side effects, and particularly does not release free formaldehyde.

Still a further important object of the present invention is directed to a new and improved nail protection preparation which is easy and fast to apply, and specifically, there can be formed a protective film along with the removal of any existing layer of nail varnish or any varnish residues in a single operation.

DETAILED DESCRIPTION OF THE INVENTION

Now in order to implement these and still further objects of the invention, there is contemplated a nail protection preparation which is composed of two separate components which are intended to be applied in sequence. One component, component No. 1, contains a polymerizable compound and the other component, component No. 2, a compound serving as polymerization catalyst. Important aspects of the nail protection preparation according to the invention reside in the features that, as a polymerizable compound, component No. 1 contains dimethylol ethylene thiourea in a quantity constituting not less than 18 percent-by-weight of the total weight of this component, a purine, water and an organic solvent or diluent or blend of solvents or diluents miscible with water and having a pH-value ranging from 8 to 10. Component No. 2, acting as a polymerization catalyst, contains 0.1n to 0.5n hydrochloric acid in a quantity sufficient to maintain within this component a pH-value of 1 to 3, and an amino acid and as a solvent or diluent a solvent or an organic solvent blend miscible with water.

The concentration of dimethylol ethylene thiourea in component No. 1 is not critical if it amounts to at least 18 percent-by-weight of the total weight of the component. The upper limit results from the solubility of dimethylol ethylene thiourea in the solvent mixture to be used, whereby a concentration of approximately 20 percent-by-weight is generally preferred. Particularly preferred as an organic solvent in component No. 1 are generally such solvent mixtures or solvents as are traditionally used as nail polish removers. Particularly efficacious has been found to be a solvent composed of acetone, ethyl acetate and ethanol in a ratio of 2 to 1 to 1.

At this point it is remarked that in the context of this disclosure the term "solvent" is used in a broader sense to encompass not only single solvents but mixtures of solvents, and the term "solvent", where appropriate, also encompasses diluents.

The addition of a purine to component No. 1 provides an additional stabilization of the dimethylol ethylene thiourea solution. A particularly suitable purine has been found to be theophylline, which is preferably added in a quantity of 0.1 to 0.2 percent-by-weight of the total weight of component No. 1.

The quantity of hydrochloric acid to be added is governed by its degree of dilution and upon the pH-value of the remaining ingredients in component No. 2; the essential governing aspect being that in component No. 2 a pH-value of from 1 to 3 must be established and maintained. The result achieved in this manner is that there is present the quantity of acid required for rapid and complete polymerization of the dimethylol ethylene thiourea.

Suitable amino acids as agents favoring film formation notably include low molecular and simple amino acids, amongst which amino acetic acid is to be especially singled out. Tests have shown that cysteine, for example, is also suitable for use as an amino acid in component No. 2. The results obtained with it have been, however, less overwhelming than those achieved with amino acetic acid as an additive.

When amino acetic acid is selected as the amino acid, the recommended quantity of additive is between 0.3 to 1 percent-by-weight of the total weight of the component, with quantities of 0.78 to 0.9 percent-by-weight of the total weight of component No. 2 being considered preferable.

Suitable as solvents miscible with water for component No. 2 are, amongst others, ethanol and acetone or a mixture thereof, or else solvent mixtures such as those used in component No. 1. Particularly preferred is a solvent mixture composed of acetone, ethyl acetate and ethanol in the proportion 2 to 1 to 1.

Furthermore, a small amount of dimethylol ethylene thiourea, for instance 0.02 percent-by-weight of the total weight of the component, may be added to component No. 2.

According to a particularly favoured compounding formula, component No. 1 contains theophylline as the purine, and as the organic solvent a mixture of acetone, ethyl acetate and ethanol in the proportion 2 to 1 to 1. The effect of using this solvent mixture, the composition of which generally resembles that of nail varnish removers, is that the application of the nail protection preparation simultaneously serves to remove existing nail polish residues, in other words, component No. 1 acts as a nail polish remover. The nail protection preparation according to the invention is preferably marketed as a combination pack in which the two components are packaged separately in such containers as small bottles, phials or bags or sachets; added to these are, possibly suitable applicators or instruments for application of the preparation, such as brushes, cotton wool swabs or non-woven towels. To be recommended particularly are combined packages with two bags or sachets, each containing a non-woven paper towel soaked in component No. 1 and component No. 2, respectively.

With the aid of such combination packs the two components can easily be applied in quick succession, whereby the application of component No. 1 will, provided a suitable solvent is selected, simultaneously removes any old remnants of nail polish. Care must be taken that all types of packaging are hermetically sealed, in order to prevent evaporation of the solvent.

A recommended procedure for the application of the nail protection preparation according to the invention is to apply component No. 1 to the nail with a suitable instrument or applicator and to remove any remaining nail varnish, then to allow a brief waiting period of a few minutes for component No. 1 to half-dry, and immediately thereafter to apply component No. 2, again by means of a suitable instrument or applicator. If desired, the process may be repeated once or several times. After a relatively short drying time there remains a thin, resistant and insoluble protective film extending over the entire surface of the treated nail. Since the structure of the protective coat is reticulate, as studies by microscope have disclosed, treated nails will not be asphyxiated even though the entire nail surface up to the nail root is covered by the film.

Use of the nail protection preparation according to the invention will not only prevent nails from becoming brittle under the effect of washing powder and other detergents and cleansing agents but, on the contrary, will cause them subjectively to exhibit a much improved elasticity after treatment and, objectively, much greater hardness than untreated nails, as has been confirmed by comparative micro-hardness tests, a point to be elaborated upon further in this disclosure.

Because the protective film resulting from the application of the inventive nail protection preparation, which is created by the polymerization of the dimethylol ethylene thiourea molecules with each other and through bridge formation between the amino groups of the keratin molecules and the methylol groups of dimethylol thiourea, is insoluble in water, the protection that is achieved is of relatively long duration and will remain intact over a protracted period of time, even after repeated contact with solvents, washing powder and detergents. In addition, the protective film may serve as a primer for colored nail polish and forms a highly adhesive, smooth and glossy surface which will also satisfy almost all aesthetic requirements.

At this point it is proposed to describe a number of practical embodiments of the present invention, which contain particularly efficient formulations, and to thereafter reproduce the results of comparative micro-hardness tests.

PRODUCTION OF THE PREPARATION

A: Solution I (Component No. 1)

The solution is produced by the intimate blending or admixing of the ingredients by vigorous stirring at room temperature, whereby either dimethylol ethylene thiourea and theophylline are first dissolved together in water and subsequently with the organic solvent, or alternatively, dimethylol ethylene thiourea is dissolved in the organic solvent and theophylline in water, whereupon both solutions are mixed together. In both cases a slightly opalescent solution was obtained.

EXAMPLE 1A

| | |
|---|---|
| Dimethylol ethylene thiourea (DMET) | 60 g (18.2 percent-by-weight) |
| Theophylline | .6 g |

| -continued | |
|---|---|
| Water | 30 ml |
| Solvent (*) | 300 ml |
| pH-value | 9.6 |

(*) Acetone to ethyl acetate to ethanol = 2 to 1 to 1

EXAMPLE 2A

| DMET | 62 g (18.8 percent-by-weight) |
|---|---|
| Theophylline | .6 g |
| Water | 30 ml |
| Solvent (*) | 300 ml |
| pH-value | 9.7 |

(*) Acetone to ethyl acetate to ethanol = 2 to 1 to 1

EXAMPLE 3A

| DMET | 64 g (19.4 percent-by-weight) |
|---|---|
| Theophylline | .65 g |
| Water | 30 ml |
| Solvent (*) | 300 ml |
| pH-value | 9.8 |

(*) Acetone to ethyl acetate to ethanol = 2 to 1 to 1

EXAMPLE 4A

| DMET | 67 g (20.3 percent-by-weight) |
|---|---|
| Theophylline | .7 g |
| Water | 30 ml |
| Solvent (*) | 300 ml |
| pH-value | 9.8 |

(*) Acetone to ethyl acetate to ethanol = 2 to 1 to 1

Solution II (Component No. 2)

The component is manufactured by dissolving amino acetic acid in water or diluted hydrochloric acid and subsequent mixing of the resulting solution with the organic solvent. In this case, too, the process took place at room temperature, with a thorough blend or admixing being obtained by vigorous stirring.

EXAMPLE 1B

| Amino acetic acid | 10 g |
|---|---|
| Water | 50 ml |
| HCl (0.5 n) | 210 ml |
| Solvent (*) | 1000 ml |
| pH-value | 2.8 to 3 |

(*) Acetone to ethyl acetate to ethanol = 2 to 1 to 1

EXAMPLE 2B

| Amino acetic acid | 20 g |
|---|---|
| Water | 100 ml |
| HCl (0.5 n) | 420 ml |
| Solvent (*) | 2000 ml |
| Colza oil | 0.0005 percent-by-weight |
| pH-value | 2.8 |

(*) Acetone to ethyl acetate to ethanol = 2 to 1 to 1

EXAMPLE 3B

| Amino acetic acid | 2.0 g |
|---|---|
| HCl (0.1 n) | 250 ml |
| Ethanol/acetone (1 to 1) | 100 ml |
| pH-value | 2.0 |

EXAMPLE 4B

| Amino acetic acid | 3.3 g |
|---|---|
| HCl (0.1 n) | 760 ml |
| Ethanol/acetone (1 to 1) | 240 ml |
| DMET | 0.1 g |
| pH-value | 1.3 |

TEST OF PROTECTIVE EFFECT ON KERATIN

A: Living nails

For the purpose of the test, finger nails were treated one to three times over a four-minute period with a solution I, the composition of which corresponded to that indicated in Examples 1A to 4A. Application was performed by means of a cotton swab. After waiting times of 1 to 3 minutes solution II, the composition of which was the same as indicated in Examples 1B to 4B, was applied. Following a drying period of 3 to 6 minutes, during which the drying process was accelerated by hot air from a hair drier, a solid, polishable film had formed which was insoluble in water and could not be scratched with a sharpened quill. It was found that the tough coat formed faster at lower pH-values of solution II. This points to the fact that polymerization of dimethylol ethylene thiourea is more rapid and complete as the concentration of acid in solution II increases.

B: Indicator test with quills

Quill sections were successively treated with solutions I and II, the composition of which was identical with that of Examples 1A to 4A and 1B to 4B. Application was performed by immersion.

On some of the quill sections treatment was repeated once or several times, whereupon the quill sections were placed in ninhydrin solution together with untreated sections. The color reaction was observed and the time required for its occurrence was recorded. The following picture emerged:

| Number of treatments | 1 | 2 | 3 | untreated |
|---|---|---|---|---|
| Color reaction (*) | ++ | + | − | +++ |
| Time for color reaction to occur (minutes) | 3 | 4 | 10 | 2 |
| (*) Negative color reaction | − | | | |
| Color reaction very weakly positive | | + | | |
| Color reaction weakly positive | | | ++ | |
| Color reaction strongly positive | | | | +++ |

The experiment demonstrated that a single treatment is sufficient to form a protective film which permits an only weak positive color reaction to take place, whereas in untreated test specimens a strongly positive reaction occurs in as little time as 2 minutes. In the specimen treated twice a merely very weak reaction was perceptible after 4 minutes, whereas in the specimen which was treated three times no reaction was observable even after 10 minutes. After the lapse of a further 60 minutes still no color reaction was perceptible. This demonstrated that after a single treatment a protective film had already formed which did not completely prevent, but largely inhibited, the reaction of keratin with ninhydrin. By repeating the treatment the protective film was reinforced, so that ultimately no reaction between keratin and ninhydrin took place.

C: Micro-hardness Tests

Measurements were carried out with the aid of a "Durimet" low-load hardness tester. The test load was 200 g, the test period 15 seconds. The measuring variable chosen was the diagonal length of the impressions in μm enlarged 100 times. Test pieces were keratin laminae from pigs' hooves cast in synthetic resin cubes. The keratin laminae were treated successively with solution I and solution II, the solutions being applied by means of non-woven paper towels soaked in one or the other of the two solutions. Solutions I and II had been prepared according to the formulas specified in Examples 1A to 4A and 1B to 4B, respectively.

The measurement results are listed in the following Table. The solutions used for individual tests are designated by the numbers of the examples under which the compositions are indicated.

1. A preparation for improving the strength of living nails, particularly the hardness of living nails, comprising:
    two separate liquid components which have to be separately stored and successively applied;
    the first of said two components containing a polymerizable compound which, when applied to the nail and after further application thereto of the second of said two components, forms a covering which covers the entire nail;
    the second of said two components containing a compound serving as a polymerization catalyst;
    said first component containing as the polymerizable compound:
    dimethylol ethylene thiourea and which is present in an amount constituting at least 18 percent-by-weight of the total weight of said first component;
    theophylline in an amount of about 0.1 to 0.2 percent-by-weight of said first component;
    water;
    a water-miscible organic solvent mixture comprising acetone, ethyl acetate and ethanol in a 2:1:1 ratio; and
    said first component having a pH-value in a range of approximately 8 to 10;
    said second component containing as the polymeriza-

TABLE

| Test specimen No. | Solution I | Waiting time *(min.) | Solution II | Drying (min.) | Temp. (°C.) | Diagonal length)** Mean value (μm) | Diagonal length)** Mean value (μm) | Differ (μm) |
|---|---|---|---|---|---|---|---|---|
| 1A/1B | 1x | 2 | 1x | 3 | 25 | 35.2 | 33.9 | 1.9 |
|  | 3x | 3 | 3x | 5 | 25 | 35.2 | 32.2 | 3.0 |
| 1A/2B | 1x | 2 | 1x | 3 | 25 | 35.4 | 32.8 | 2.6 |
|  | 3x | 3 | 3x | 5 | 25 | 35.4 | 32.1 | 3.3 |
| 1A/3B | 1x | 2 | 1x | 3 | 25 | 35.4 | 33.1 | 2.3 |
|  | 3x | 3 | 3x | 5 | 25 | 35.4 | 32.0 | 3.4 |
| 1A/4B | 1x | 2 | 1x | 3 | 25 | 35.5 | 32.9 | 2.6 |
|  | 3x | 3 | 3x | 5 | 25 | 35.5 | 31.8 | 3.7 |
| 2A/1B | 1x | 2 | 1x | 3 | 25 | 34.6 | 33.2 | 1.4 |
|  | 3x | 3 | 3x | 5 | 25 | 35.9 | 33.5 | 2.4 |
| 2A/2B | 1x | 2 | 1x | 3 | 25 | 37.1 | 35.3 | 1.8 |
|  | 3x | 3 | 3x | 5 | 25 | 35.8 | 32.6 | 3.2 |
| 2A/3B | 1x | 2 | 1x | 3 | 25 | 37.0 | 33.8 | 3.2 |
|  | 3x | 3 | 3x | 5 | 25 | 36.5 | 32.2 | 4.3 |
| 2A/4B | 1x | 2 | 1x | 3 | 25 | 37.0 | 33.6 | 3.4 |
|  | 3x | 3 | 3x | 5 | 25 | 36.2 | 32.2 | 4.0 |
| 3A/1B | 1x | 2 | 1x | 3 | 25 | 35.9 | 33.5 | 2.4 |
|  | 3x | 3 | 3x | 5 | 25 | 35.9 | 32.2 | 3.7 |
| 3A/2B | 1x | 2 | 1x | 3 | 25 | 35.8 | 33.2 | 2.6 |
|  | 3x | 3 | 3x | 5 | 25 | 35.8 | 32.0 | 3.8 |
| 3A/3B | 1x | 2 | 1x | 3 | 25 | 35.6 | 33.1 | 2.5 |
|  | 3x | 3 | 3x | 5 | 25 | 35.6 | 32.0 | 3.6 |
| 3A/4B | 1x | 2 | 1x | 3 | 25 | 35.5 | 32.8 | 2.7 |
|  | 3x | 3 | 3x | 5 | 25 | 35.5 | 31.6 | 3.9 |
| 4A/1B | 1x | 2 | 1x | 3 | 25 | 35.6 | 33.2 | 2.4 |
|  | 3x | 3 | 3x | 5 | 25 | 35.6 | 32.2 | 3.6 |
| 4A/2B | 1x | 2 | 1x | 3 | 25 | 36.7 | 33.9 | 2.8 |
|  | 3x | 3 | 3x | 5 | 25 | 36.3 | 32.6 | 3.7 |
| 4A/3B | 1x | 2 | 1x | 3 | 25 | 36.2 | 32.8 | 3.4 |
|  | 3x | 3 | 3x | 3 | 50 | 36.3 | 32.2 | 4.1 |
| 4A/4B | 1x | 2 | 1x | 3 | 25 | 37.0 | 33.6 | 3.4 |
|  | 3x | 3 | 3x | 3 | 50 | 36.5 | 32.5 | 4.0 |

*Waiting time between treatments with solutions I and II
**Diagonal length of impressions, enlarged 100 times While there are described present preferred embodiments of the invention, it is to be distinctly understood that the invention is not limited thereto, but may be otherwise variously embodied and practiced within the scope of the following claims. ACCORDINGLY,
What I claim is:

tion catalyst:
    0.1n to 0.5n hydrochloric acid in a quantity sufficient to adjust and maintain a pH-value in the range of 1 to 3 in said second component;
    amino acetic acid as an agent favoring film formation in an amount of about 0.3 to 1.0 percent-by-weight of said second component; and a water-miscible organic solvent mixture comprising acetone, ethyl acetate and ethanol in a 2:1:1 ratio.

2. The preparation as defined in claim 1, wherein:
said first component possesses a pH-value of about 9.6 and has the following composition:

| | |
|---|---|
| dimethylol ethylene thiourea | 60 gm |
| theophylline | 0.6 gm |
| water | 30 ml |
| mixture of acetone, ethyl acetate and ethanol (2:1:1) | 300 ml; and | said second component possessing a pH-value of approximately 2.8 to 3 and possessing the following composition:

| | |
|---|---|
| amino acetic acid | 10 gm |
| water | 50 ml |
| 0.5 n hydrochloric acid | 210 ml |
| mixture of acetone, ethyl acetate and ethanol (2:1:1) | 1000 ml. |

3. The preparation as defined in claim 1, wherein:
said first component possesses a pH-value of about 9.6 and has the following composition:

| | |
|---|---|
| dimethylol ethylene thiourea | 60 gm |
| theophylline | 0.6 gm |
| water | 30 ml |
| mixture of acetone, ethyl acetate and ethanol (2:1:1) | 300 ml; and | and
said second component possesses a pH-value of about 2.0 and has the following composition:

| | |
|---|---|
| amino acetic acid | 0.2 gm |
| 0.1 n hydrochloric acid | 25 ml |
| ethanol | 5 ml |
| acetone | 5 ml. |

4. The preparation as defined in claim 1, wherein:
said first component possesses a pH-value of about 9.6 and has the following composition:

| | |
|---|---|
| dimethylol ethylene thiourea | 60 gm |
| theophylline | 0.6 gm |
| water | 30 ml |
| mixture of acetone, ethyl acetate and ethanol (2:1:1) | 300 ml; and | and
said second component possessing a pH-value of approximately 1.3 and has the following composition:

| | |
|---|---|
| amino acetic acid | 3.33 gm |

| -continued | |
|---|---|
| 0.1 n hydrochloric acid | 760 ml |
| ethanol | 120 ml |
| acetone | 120 ml |
| dimethylol ethylene thiourea | 0.15 gm. |

5. The preparation as defined in claim 1, wherein:
said preparation is present in the form of a combination package composed of two sachets hermetically sealed to prevent solvent evaporation;
the first sachet containing a non-woven fabric impregnated with the first component; and
the second sachet containing a non-woven fabric impregnated with the second component.

6. The preparation as defined in claim 1, wherein:
said preparation is present in the form of a combination package composed of two flasks hermetically sealed to prevent solvent evaporation;
one of said flasks containing the first component; and
the other of said flasks containing the second component.

7. The preparation as defined in claim 1, wherein:
said first component has a pH-value in the range of about 9.6 to 9.8; and
said second component has a pH-value in the range of about 1.3 to 3.

8. A method of strengthening living nails, especially hardening living nails, comprising the steps of:
applying a solution thinly and uniformly to a nail to be treated, wherein said solution contains dimethylol ethylene thiourea in a quantity constituting at least 18 percent-by-weight of the total weight of the solution, theophylline in a quantity constituting about 0.1 to 0.2 percent-by-weight of the solution, water and a water-miscible organic solvent mixture comprising acetone, ethyl acetate and ethanol in a 2:1:1 ratio, said solution having a pH-value in the range of 8 to 10;
drying the solution until there is formed a protective layer;
thereafter applying to the thus treated nail a component which causes the polymerization of the dimethylol ethylene thiourea present in the previously formed protective layer;
said component containing 0.1n to 0.5n hydrochloric acid in a quantity sufficient to adjust and maintain a pH-value in the range of 1 to 3 in said component, amino acetic acid as an agent favoring film formation in a quantity constituting about 0.3 to 1.0 percent-by-weight of said component and a water-miscible organic solvent mixture comprising acetone, ethyl acetate and ethanol in a 2:1:1 ratio;
said component being applied so as to cause complete polymerization of the dimethylol ethylene thiourea present in the previously formed protective layer and to form a covering which covers the entire nail; and
allowing the thus formed covering to dry until completely dried while forming a fixedly adhering protective layer which is insoluble in water and organic solvents and resistant to mechanical load.

* * * * *